United States Patent
Grausam et al.

(10) Patent No.: US 11,541,355 B2
(45) Date of Patent: *Jan. 3, 2023

(54) METHOD FOR DETERMINING A PERMEATION PROPERTY OF HOLLOW FIBRE MEMBRANE BUNDLES

(71) Applicant: FRESENIUS MEDICAL CARE DEUTSCHLAND GMBH, Bad Homburg (DE)

(72) Inventors: Elmar Grausam, St. Wendel (DE); Ingo Fehr, Bonn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 49 days.

This patent is subject to a terminal disclaimer.

(21) Appl. No.: 17/358,025

(22) Filed: Jun. 25, 2021

(65) Prior Publication Data

US 2021/0316252 A1   Oct. 14, 2021

Related U.S. Application Data

(63) Continuation of application No. 16/343,415, filed as application No. PCT/EP2017/076959 on Oct. 23, 2017, now Pat. No. 11,052,350.

(30) Foreign Application Priority Data

Oct. 24, 2016  (DE) .................... 10 2016 012 722.8

(51) Int. Cl.
*B01D 63/10* (2006.01)
*B01D 63/02* (2006.01)
(Continued)

(52) U.S. Cl.
CPC ............ *B01D 63/021* (2013.01); *A61M 1/16* (2013.01); *A61M 1/1621* (2014.02);
(Continued)

(58) Field of Classification Search
CPC .. B01D 63/021; B01D 65/10; B01D 2313/04; B01D 2323/42; A61M 1/16; A61M 1/1621; A61M 2205/3379; A61M 2207/00
See application file for complete search history.

(56) References Cited

U.S. PATENT DOCUMENTS

| | | | |
|---|---|---|---|
| 4,678,573 A | 7/1987 | Otstot et al. | |
| 5,110,477 A | 5/1992 | Howard et al. | |

(Continued)

FOREIGN PATENT DOCUMENTS

| | | |
|---|---|---|
| CN | 102967543 A | 3/2013 |
| CN | 204320109 U | 5/2015 |

(Continued)

OTHER PUBLICATIONS

International Search Report and Written Opinion issued in corresponding International Patent Application No. PCT/EP2017/076959 (with English translation of International Search Report) dated Jan. 16, 2018 (15 pages).

(Continued)

*Primary Examiner* — Waqaas Ali
(74) *Attorney, Agent, or Firm* — Kilyk & Bowersox, P.L.L.C.

(57) ABSTRACT

The invention relates to a method of determining a permeation property of hollow-fibre membranes wherein the permeation property of the hollow-fibre membrane is determined on a hollow-fibre membrane bundle which has been introduced into a housing and has terminally open hollow-fibre membranes at a first end of the hollow-fibre membrane bundle and terminally closed hollow-fibre membranes at a (Continued)

Figure 1:
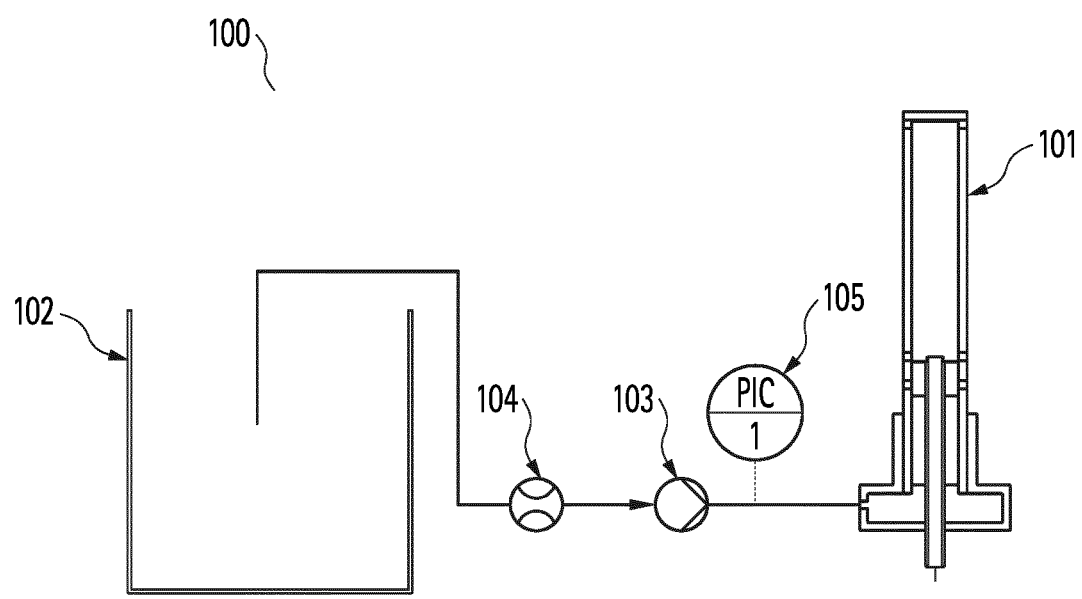

second end of the hollow-fibre membrane bundle. The invention more particularly relates to a method of determining the ultrafiltration rate and/or the ultrafiltration coefficient of hollow-fibre membranes.

21 Claims, 4 Drawing Sheets

(51) Int. Cl.
  *B01D 65/10* (2006.01)
  *A61M 1/16* (2006.01)
(52) U.S. Cl.
  CPC ..... *B01D 65/10* (2013.01); *A61M 2205/3379* (2013.01); *A61M 2207/00* (2013.01); *B01D 2313/04* (2013.01); *B01D 2323/42* (2013.01)

(56) References Cited

U.S. PATENT DOCUMENTS

| | | | |
|---|---|---|---|
| 6,065,329 A * | 5/2000 | Fukada | B01D 65/102 73/40 |
| 2003/0155294 A1 | 8/2003 | Heilmann et al. | |
| 2008/0017029 A1 | 1/2008 | Kase et al. | |
| 2010/0051180 A1 | 3/2010 | Barra et al. | |
| 2016/0023169 A1 | 1/2016 | Krause et al. | |
| 2019/0240625 A1 | 8/2019 | Grausam et al. | |
| 2019/0247798 A1 | 8/2019 | Grausam et al. | |

FOREIGN PATENT DOCUMENTS

| | | |
|---|---|---|
| DE | 102013203082 A1 | 8/2014 |
| EP | 0958852 A1 | 11/1999 |
| EP | 2418012 A1 | 2/2012 |
| JP | H04-150926 A | 5/1992 |
| JP | 2007-216175 A | 8/2007 |
| JP | 201116116 A | 1/2011 |
| JP | 2015150349 A | 8/2015 |
| JP | 2019532809 A | 11/2019 |
| WO | 2013034611 A1 | 3/2013 |
| WO | 2013176140 A1 | 11/2013 |
| WO | 2015014934 A1 | 2/2015 |

OTHER PUBLICATIONS

International Preliminary Report on Patentability issued in corresponding International Patent Application No. PCT/EP2017/076959 dated Apr. 30, 2019 (8 pages).

Serra et al., "Dead-end ultrafiltration in hollow fiber modules: Module design and process simulation," Journal of Membrane Science, 1998, vol. 145, pp. 159-172 (14 pages).

Ahmed et al., "Use of sealed end hollow fibers for bubbleless membrane aeration: experimental studies," Journal of Membrane Science, 1992, vol. 69, pp. 1-10 (10 pages).

* cited by examiner

METHOD FOR DETERMINING A PERMEATION PROPERTY OF HOLLOW FIBRE MEMBRANE BUNDLES

This application is a continuation of U.S. patent application Ser. No. 16/343,415, filed Apr. 19, 2019, which is a National Stage Application of PCT/EP2017/076959, filed Oct. 23, 2017, which claims priority to German Patent Application No. 10 2016 012 722.8, filed Oct. 24, 2016.

FIELD OF THE INVENTION

The invention relates to a method of determining a permeation property of hollow-fibre membranes in a hollow-fibre membrane bundle. More particularly, the invention relates to a method of determining the ultrafiltration coefficient of hollow-fibre membranes in a hollow-fibre membrane bundle from an ascertained permeation property.

The invention further relates to an apparatus for carrying out a method of determining a permeation property, in particular determining the ultrafiltration rate, of hollow-fibre membranes in a hollow-fibre membrane bundle.

The invention further relates to a method of forming hollow-fibre membrane filter modules from hollow-fibre membranes having at least one predetermined permeation property, in particular a predetermined ultrafiltration rate.

BACKGROUND OF THE INVENTION

Hollow-fibre membranes are widely used in the purification of liquids. More particularly, hollow-fibre membranes are employed in biomedical engineering for water treatment and blood cleansing, particularly in the dialysis of renally insufficient patients. Hollow-fibre membranes of this type are assembled as hollow-fibre membrane bundles into filter modules. Such filter modules for blood cleansing have come to be formed on a mass production scale.

The construction of hollow-fibre membrane filter modules and the production of hollow-fibre membranes for dialysis are known in the prior art (Uhlenbusch-Körwer, Bonnie-Schorn, Grassmann, Vienken, "Understanding Membranes and Dialysers" Publisher: Pabst Science Publishers, 2004).

Hollow-fibre membranes used for blood cleansing frequently consist of polysulphone (PSU) and polyvinylpyrrolidone (PVP) and are generally produced in a dry-wet spinning process. In processes of this type, a spinning solution containing the polymers PSU and PVP and a solvent is extruded through an annular die to spin a hollow filament. The spun filament is initially led perpendicularly through an air gap. Concurrently with the extrusion of the spun filament, a coagulation medium is extruded into the lumen of the spun filament so that a coagulation process ensues with the extrusion of the spun filament. Coagulation is accompanied by phase inversion to form sol and gel phases within the spun filament. After passing through the air gap, the spun filament is introduced into a coagulation bath where the coagulation of the spun filament is completed to form the solid structure of a hollow-fibre membrane. The hollow-fibre membrane obtained then passes through a plurality of rinse baths and drying zones. The hollow-fibre membranes obtained differ in pore structure and properties according to pre-set spinning conditions. The term "PSU" herein is to be understood as a generic term for any polymers with sulphone groups, including for example polyether sulphone and polyphenyl sulphone and copolymers comprising same.

In general, a multiplicity of hollow-fibre membranes are extruded simultaneously and concurrently in a production plant so that the hollow-fibre membrane fibres obtained after passing through the production plant are combinable into a filament sheet or fibre bundle and are taken up by a reel. Corresponding processes are known in the prior art and have, for example, been described in DE 10 2006 057 101 A1.

The process for forming hollow-fibre membranes is a continuous process run as a three-shift operation in the production facilities. There is accordingly a constant need to monitor the quality of the fibres obtained in order to avoid faulty production to any significant extent. Tests are therefore carried out on a continuous basis to check whether the properties of the hollow-fibre membrane obtained are on spec and the production process is proceeding in accordance with the pre-set conditions.

Hollow-fibre membranes are characterized via their permeation properties in particular. The permeation property of a hollow-fibre membrane determines whether the hollow-fibre membrane is usable for certain types of separation process, for example in the dialysis of renally insufficient patients. The determination of a permeation property of hollow-fibre membranes hitherto required first having to assemble the hollow-fibre membrane bundles obtained into filter modules before the separation properties of the membrane could be ascertained.

To construct a filter, the hollow-fibre membrane bundle has to be impressed into a filter housing and terminally potted. The potting compounds are curable resins, in particular polyurethane. Potting and curing are time-consuming operations, so filter construction and the subsequent analyses on the filters in the plant labs may take several hours. All the while, hollow-fibre membranes continue to be produced. In the extreme case, analytical results some hours later will show that the hollow-fibre membrane obtained is no longer on spec, so the manufacturing output of several hours has to be discarded.

When, by contrast, the analytical results show that the hollow-fibre membranes obtained do meet the specifications, the corresponding output in terms of manufactured hollow-fibre membranes may be further processed into the corresponding filter modules.

As mentioned above, hollow-fibre membrane filter modules of this type are used for the haemodialysis of renally insufficient patients. The haemodialysis of renally insufficient patients is based on the principle of the transmembrane type of mass transfer. In haemodialysis, blood flows along the inside surface of hollow-fibre membranes, while an appropriate type of dialysis liquid flows on the outside surface of the hollow-fibre membranes. The liquids flow in opposite directions, giving rise to a countercurrent type of filtration.

Depending on the filtration conditions in blood treatments of renally insufficient patients, undesirable metabolites such as, for example, urea, creatinine, phosphate and harmful types of plasma proteins are removed from a patient's blood by permeating through the membrane wall and are possibly taken up by the dialysis liquid. Similarly, dissolved constituents of the dialysis liquid may also permeate through the membrane wall onto the blood side. The dialysis liquid is provided as an aqueous physiological solution containing, for example, electrolytes (e.g. $Na^+$, $K^+$, $Mg^{2+}$, $Ca^{2+}$, $Cl^-$), glucose and a buffer (e.g. $NaHCO_3$).

The transmembrane type of mass transfer in the above-outlined scheme of haemodialysis or blood cleansing may in principle take place in two ways, by convective transfer or diffusive transfer.

In convective transfer, liquid, and substances present therein, permeates through the membrane along a transmembrane pressure gradient. In diffusive transfer, substances permeate through the membrane by virtue of the dissolved substances' intrinsic molecular motion and a concentration gradient across the membrane wall.

Depending on the type of the hollow-fibre membrane and/or the pore size of the hollow-fibre membrane and the established rate of flow for blood and dialysate, the filtration process may proceed in one way or the other. When, for example, the blood treatment in a haemofiltration or haemodiafiltration process utilizes hollow-fibre membranes having large relatively large pores and/or high flowrates are preset for the two streams of liquid—blood and dialysate—at least part of the filtration will proceed convectively.

When, by contrast, the blood treatment takes the form of a simple dialysis, membranes having smaller pores are used and the mass transfer is essentially diffusive. Under these conditions it is particularly just low molecular weight substances which permeate, examples being urea, electrolytes, vitamin B12, creatinine and phosphate.

Yet the clearance of harmful types of plasma proteins from the blood of renally insufficient patients is only achievable in therapeutic processes where a convective type of mass transfer is made possible. Plasma proteins of this type occur in the so-called middle-molecular range of the plasma proteins. Familiar proteins in the middle-molecular range are β-2 microglobulin or interleukin-6.

Depending on the pore size, the ultrafiltration coefficient is a further permeation property of hollow-fibre membranes. The ultrafiltration coefficient, in a given filtration build, indicates the permeability of the hollow-fibre membrane to a liquid, generally water, per unit time per unit pressure difference. Methods of determining the ultrafiltration coefficient of hollow-fibre membranes are known in the prior art. The DIN/EN/ISO 8637:2014 standard is referenced in this regard. Said standard describes the use of blood as test liquid. However, in a departure from the standard, water or blood plasma is frequently used as test liquid. Particularly water is widely available, greatly simplifying the measurement. The ultrafiltration coefficient is therefore also referred to as "aqueous".

An unintended change in a parameter during the manufacture of hollow-fibre membranes may affect the phase inversion process. As a result, mean pore size or the number of pores per unit membrane area may change, which directly affects the detectable ultrafiltration. In the manufacture of hollow-fibre membranes, therefore, it is particularly the specified ultrafiltration rate of a hollow-fibre membrane which is important in order to be able to supervise the production process.

The prior art discloses a method of determining a permeation property of hollow-fibre membranes which is described in WO 2013/034611. WO 2013/034611 A1 at page 18 describes a method of determining the hydraulic permeability on a terminally potted hollow-fibre membrane bundle.

It has transpired that existing methods of quality control in the manufacture of hollow-fibre membranes are in need of improvement. The invention accordingly has for its object to provide a simplified method of determining a permeation property, particularly the ultrafiltration rate of hollow-fibre membranes.

The invention further has for its object to provide an apparatus for testing hollow-fibre membrane bundles to determine the ultrafiltration rate of the hollow-fibre membranes.

The invention further has for its object to provide a method of manufacturing hollow-fibre membranes whereby hollow-fibre membranes are manufacturable within a production process such that the specifications regarding a permeation property of the hollow-fibre membranes, particularly the ultrafiltration rate, are complied with.

SUMMARY OF THE INVENTION

In a first aspect of the invention, it was found that, surprisingly, the stated problems of determining a permeation property are solved by providing a method according to claim 1. Claims 2 to 17 set forth preferred embodiments of the invention from the first aspect.

It was further found, in a second aspect of the invention, that the problems described are solved by an apparatus according to claim 18, while claims 19 and 20 set forth preferred embodiments of the invention according to a second aspect.

In a third aspect, the invention provides a method of manufacturing hollow-fibre membrane filter modules according to claim 21 by using a method as per any one embodiment from 1 to 17.

DETAILED DESCRIPTION OF THE INVENTION

It was found in a first aspect of the invention that, surprisingly, the aforementioned problem is solved by a method of determining at least one permeation property, more particularly the ultrafiltration rate, of hollow-fibre membranes. The method comprises the steps of providing a hollow-fibre membrane bundle comprising a multiplicity of hollow-fibre membranes having a first end and a second end, wherein the lumens of the hollow-fibre membranes at the first end of the hollow-fibre membrane bundle are terminally open, more particularly liquid-permeable, and at the second end of the hollow-fibre membrane bundle are terminally closed, more particularly liquid-tight, providing a housing for receiving the hollow-fibre membrane bundle having a first end and a second end, wherein the first end has at least one liquid inlet, introducing the hollow-fibre bundle into the housing, wherein the first end of the hollow-fibre bundle having the terminally open lumens of the hollow-fibre membranes is oriented towards the at least one liquid inlet at the first end of the housing, determining a permeation property of the hollow-fibre membranes.

It transpired that the method steps specified make it possible to determine permeation properties of hollow-fibre membranes without first having to form hollow-fibre membrane filter modules from the hollow-fibre membrane bundles. There is accordingly no need for the burdensome formation of test filter modules. The permeation property of the hollow-fibre membrane is determined without first potting the hollow-fibre membrane bundle.

In one embodiment, the method of the invention comprises the steps of providing a hollow-fibre membrane bundle comprising a multiplicity of hollow-fibre membranes having a first end and a second end, wherein the lumens of the hollow-fibre membranes at the first end of the hollow-fibre membrane bundle are terminally open, more particularly liquid-permeable, and at the second end of the hollow-fibre membrane bundle are terminally closed, more particularly liquid-tight, providing a housing for receiving the hollow-fibre membrane bundle having a first end and a second end, wherein the first end has at least one liquid inlet, introducing the hollow-fibre bundle into the housing, wherein the first end of the hollow-fibre bundle having the terminally open lumens of the hollow-fibre membranes is oriented towards the at least one liquid inlet at the first end of the housing, providing at least one compression apparatus (204, 340, 450, 451, 460, 461) for compressing the hollow-fibre membrane bundle in at least a subregion (222, 322) of the hollow-fibre membrane bundle, more particularly for compressing the hollow-fibre membrane bundle subregion adjoining the first end of the hollow-fibre membrane bundle, providing at least one liquid outlet (204, 340, 440), providing at least one test liquid, inflowing the at least one test liquid through the at least one liquid inlet (212, 312, 412) at the first end of the housing (101, 201, 301, 401) into the interior of the housing and/or of the hollow-fibre membrane bundle and/or of the hollow-fibre membranes (420, 421), compressing the hollow-fibre membrane bundle in at least a subregion of the hollow-fibre membrane bundle (222, 322), more particularly compressing the hollow-fibre membrane bundle subregion adjoining the first end of the hollow-fibre membrane bundle by means of the at least one compression apparatus (203, 340, 450, 451, 460, 461), determining the ultrafiltration rate and/or the ultrafiltration coefficient of the hollow-fibre membranes by recording at least one measured value, more particularly by measuring the emerging amount of the at least one test liquid at at least one liquid outlet.

It transpired that the recording of the at least one measured value, more particularly the recording of the value of the emerging amount of the at least one test liquid at the at least one liquid outlet is representative of a permeation property of the tested hollow-fibre membrane in the hollow-fibre membrane bundle. The method makes it possible to determine the permeation property of the hollow-fibre membranes without first having to form hollow-fibre membrane filter modules from the hollow-fibre membrane bundles. There is accordingly no need for the burdensome formation of test filter modules.

To form prior art hollow-fibre membrane filter modules, corresponding hollow-fibre membrane bundles are impressed into a housing of a filter module and terminally potted with a casting resin in the housing. The interspace between the fibres is filled with the casting resin in the process so that terminally no liquid can penetrate through the interspace between the fibres. Initially, the lumens of the hollow-fibre membranes are also closed at the ends. The lumens of the hollow-fibre membranes are bared again by terminally separating off a part of the potted encapsulation. The method of the invention has the advantage that the terminal potting of the hollow-fibre membrane bundle is dispensable. In the context of the present invention, the hollow-fibre membranes merely have to be closed at one end.

A further effect of the invention according to the first aspect resides in the fact that the hollow-fibre membranes are testable for their permeation property within a short time, i.e. within a few minutes of having been formed. Prior art test procedures, for which it is necessary to build complete test filter modules, take a period of at least 3 hours. The large amount of scrap which can be produced during this period is avoidable by using the method of the invention. It is thereby possible, for example during the production process of hollow-fibre membranes, to quickly make deductions about the quality of the production process and take any appropriate measures to control the production process without time delay. The method of the invention thus has the advantage of being quick and reliable in delivering results for controlling the production of hollow-fibre membranes. Any significant faulty production is avoidable as a result.

In one embodiment of the method according to the invention, the method consists of the following steps:

providing a hollow-fibre membrane bundle comprising a multiplicity of hollow-fibre membranes having a first end and a second end, wherein the lumens of the hollow-fibre membranes at the first end of the hollow-fibre membrane bundle are terminally open, more particularly liquid-permeable, and at the second end of the hollow-fibre membrane bundle are terminally closed, more particularly liquid-tight, providing a housing for receiving the hollow-fibre membrane bundle having a first end and a second end, wherein the first end has at least one liquid inlet, introducing the hollow-fibre bundle into the housing, wherein the first end of the hollow-fibre bundle having the terminally open lumens of the hollow-fibre membranes is oriented towards the at least one liquid inlet at the first end of the housing, providing at least one compression apparatus (204, 340, 450, 451, 460, 461) for compressing the hollow-fibre membrane bundle in at least a subregion (222, 322) of the hollow-fibre membrane bundle, more particularly for compressing the hollow-fibre membrane bundle subregion adjoining the first end of the hollow-fibre membrane bundle, providing at least one liquid outlet (204, 340, 440), providing at least one test liquid, inflowing the at least one test liquid through the at least one liquid inlet (212, 312, 412) at the first end of the housing (101, 201, 301, 401) into the interior of the housing and/or of the hollow-fibre membrane bundle and/or of the hollow-fibre membranes (420, 421), compressing the hollow-fibre membrane bundle in at least a subregion of the hollow-fibre membrane bundle (222, 322), more particularly compressing the hollow-fibre membrane bundle subregion adjoining the first end of the hollow-fibre membrane bundle by means of the at least one compression apparatus (203, 340, 450, 451, 460, 461), determining the ultrafiltration rate and/or the ultrafiltration coefficient of the hollow-fibre membranes by recording at least one measured value, more particularly by measuring the emerging amount of the at least one test liquid at at least one liquid outlet.

A first step of the method according to the invention comprises providing a hollow-fibre membrane bundle comprising a multiplicity of hollow-fibre membranes having a first end and a second end, wherein the openings of the lumens of the hollow-fibre membranes at the first end of the hollow-fibre membrane bundle are terminally open, more particularly liquid-permeable, and at the second end of the hollow-fibre membrane bundle are terminally closed, more particularly liquid-tight.

The term "hollow-fibre membrane bundle" herein is to be understood as meaning a bundle formed from a multiplicity of hollow-fibre membranes. A "hollow-fibre membrane" has a capillary structure. More particularly, the hollow-fibre membrane is a membrane in the shape of a hollow filament which consists of a porous material and has an essentially circular diameter. The wall thicknesses of such hollow-fibre membranes as may be provided for dialysis may be in the range from 10 to 100 µm, depending on membrane material. Lumen diameters with hollow-fibre membranes of this type are commonly between 150 µm to 250 µm, in particular between 180 µm and 220 µm, while fibre length is in the range from 150 µm to 300 mm, in particular between 250 mm and 300 mm. Liquids are able to flush through this bore of hollow-fibre membranes. Hollow-fibre membranes are more particularly provided for separation processes reliant on a transmembrane permeation of matter from the outside surface to the hollow interior, or from the hollow interior to the outside surface, of the hollow-fibre membrane. Hollow-fibre membranes of this type are typically employed in the therapeutic treatment of blood.

The material of a hollow-fibre membrane may be selected from polymers, preferably from polysulphone, polyether sulphone, polyvinylpyrrolidone, polypropylene, polyacrylonitrile, polyamide, polyethylene ether, cellulose, cellulosic regenerate, cellulose acetate or mixtures thereof. Particular preference is given to membranes comprising, more particularly consisting of, a hydrophobic polymeric material, e.g. polysulphone or polyether sulphone, and a hydrophilic polymeric material, e.g. polyvinylpyrrolidone. Hollow-fibre membranes are engineered such that the membrane material has a multiplicity of pores designed to enable mass transfer between the interior of the hollow-fibre membrane and the surroundings of the hollow-fibre membrane and, more particularly, to enable a selective type of mass transfer according to the size of the particles of the particular matter. "Lumen" is the name given to the hollow interior of a hollow-fibre membrane.

For the purposes of the present invention, the term "lumen" is to be understood as meaning a coherent cavity extending in the interior of the hollow-fibre membrane all the way from the first end to the second end of the hollow-fibre membrane. The lumen of hollow-fibre membranes is surrounded by the porous membrane wall, so liquids and/or gases routed through the interior of the lumen are in mass-transfer contact with the membrane wall along the hollow-fibre membrane and a transmembrane passage of fluids is observable. The openings to the lumens at the fibre ends constitute access points where matter, more particularly liquids and/or gases is able to flow into the fibre interior and/or out again.

The act of combining a plurality of hollow-fibre membranes into a hollow-fibre membrane bundle leads to the creation, between the individual hollow-fibre membranes, of interspaces likewise capable of ducting liquids and/or gases. A hollow-fibre membrane bundle preferably numbers at least 50 to 20 000 hollow-fibre membranes. Typical diameters of hollow-fibre membrane bundles are in the range from 15 mm to 50 mm. The hollow-fibre membrane bundle employed in the method of the invention is unpotted, i.e. the ends of the hollow-fibre membrane bundle are not potted in a casting resin.

The act of combining a multiplicity of hollow-fibre membranes into a hollow-fibre membrane bundle results in a package of hollow-fibre membranes wherein the hollow-fibre membranes are packed together at a packing density predetermined by the package. Hollow-fibre membrane bundles develop a resistive force in such a package. As a result, a hollow-fibre membrane bundle is compressible and offers a restoring force in response to compression. Compressed hollow-fibre membrane bundles want to return to a relaxed state. The restoring force is more particularly also connected with a wave pattern embossed on the hollow-fibre membranes in the course of their formation. Corresponding methods of forming hollow-fibre membranes and hollow-fibre membrane bundles are known from the prior art, for example from DE 100 07 327 A1.

Hollow-fibre membrane bundles as employed in the method of the invention further have a first end and a second end, the first end being different from the second end.

In the method of the present invention, the hollow-fibre membrane bundle has closed hollow-fibre membranes at the second end. More particularly, the openings of the lumens of the hollow-fibre membranes at the second end of the hollow-fibre membrane bundle are terminally closed, more particularly such that no liquid and/or gas will terminally exit from the lumen into the surroundings or enter the lumen from the surroundings.

Procedures for closing the hollow-fibre membranes at one end of the hollow-fibre membrane bundle are known in the prior art. The hollow-fibre membranes are closable by application of heat, for example via heat radiation or heat contact, by means of resins, or via laser radiation. A method involving heat contact against an aluminium foil is preferable in the present invention. For example, a hotplate at 250° C. to 350° C. may be used to melt a hollow-fibre membrane bundle on one side at the ends of the hollow-fibre membranes. An aluminium foil positioned as a release liner between the hotplate and the ends of the hollow-fibre membranes is removable back off the end of the hollow-fibre membrane bundle, after cooling down, by peeling. The melting process on the hotplate causes the openings of the lumens at the ends of the hollow-fibre membranes to melt together. This results in a liquid-tight closure on the first ends of the hollow-fibre membranes.

A further step of the method according to the invention comprises providing a housing for receiving the hollow-fibre membrane bundle having a first end and a second end, wherein the first end has at least one liquid inlet.

The term "housing" herein is to be understood as meaning a hollow body provided for receiving a multiplicity of hollow-fibre membranes. When a hollow-fibre membrane bundle consisting of a multiplicity of hollow-fibre membranes is introduced into a housing, this leaves a space in the housing, between the hollow-fibre membranes and between the housing's inner wall and the outside surface of the hollow-fibre membranes, wherethrough liquids are able to flow. Suitable housings may have an elongated shape, so one dimension of a housing is longer than the second and third dimensions and hence is termable the longitudinal axis of the housing. In accordance with the longitudinal shape of the provided housing, it is usable in preferred orientations, vertically and horizontally.

In one preferred shape, such a housing is cylindrical, for example in sleeve form. Corresponding sleeve-shaped housings may be open at one end at least, so a hollow-fibre membrane bundle is introduceable into the sleeve. The housing is subsequently closable or combinable with corresponding end-caps or connectors. Corresponding sleeves useful as housings for hollow-fibre membrane bundles are known in the prior art from the construction of dialysers. Corresponding housings preferably consist of a flexurally stiff plastics material, e.g. polycarbonate, polypropylene or polyoxymethylene, or of metals, e.g. aluminium or stainless steel.

In the method of the present invention, the housing has at least one first liquid inlet at one end of the housing. The liquid inlet is designed to let liquid flow into the interior of the housing and/or into the interior of the hollow-fibre membrane bundle/hollow-fibre membranes. The at least one liquid inlet may constitute a cylindrical point of access to the housing at that end of the housing. However, the point of access for liquid may also constitute an open end of a cylindrical housing.

The method of the invention further provides at least one liquid outlet spaced apart from the at least one liquid inlet. "Spaced apart" herein is to be understood as meaning that the liquid inlet and the liquid outlet are sufficiently remote from each other that liquid inflowing through the liquid inlet will flow through a part of the housing and/or a part of the hollow-fibre membrane bundle. It is more particularly provided in this connection that the liquid will flow through a housing part for receiving a hollow-fibre membrane bundle. The liquid outlet more particularly serves to route away permeate, more particularly ultrafiltrate.

A further step of the method according to the invention comprises providing at least one compression apparatus capable of compressing hollow-fibre membrane bundles in at least a subregion of the hollow-fibre membrane bundle. Hollow-fibre membrane bundles are deformable and, more particularly, compressible. On compression, the packing density of the hollow-fibre membranes in the hollow-fibre membrane bundle increases. Packing density here refers to the degree of compactness of hollow-fibre membranes in a hollow-fibre membrane bundle which has been introduced into a housing. The packing density of hollow-fibre membranes is the sum total of the cross-sectional areas of the individual hollow-fibre membranes, divided by the overall cross-sectional area enclosing all the hollow-fibre membrane cross-sectional areas in an assembly. This is generally the housing cross-section. In the case of hollow-fibre membranes and housing geometries having a circularly round cross-section, the packing density computes according to the following formula:

$$\delta_{(packing\ density)} = n \cdot \frac{d^2_{(fibre)}}{d^2_{(housing)}}$$

$d_{(fibre)}$: is the average outside diameter of the unstressed hollow-fibre membrane
$d_{(filter)}$: is the inside diameter of the housing
n: is the number of hollow-fibre membranes in the housing
The term "unstressed hollow-fibre membrane" refers to an individual free hollow-fibre membrane. In the housing, the hollow-fibre membranes may become deformed, i.e. assume a deformed cross-section, under the stress imposed by a compressive effect. More particularly, packing densities greater than 100% may be obtained as a result. However, the packing density is always computed on the basis of the diameter of the unstressed hollow-fibre membrane.

The "compression apparatus" used is a means that is capable of increasing the packing density of the hollow-fibre membranes in the hollow-fibre membrane bundle. Compression apparatuses capable of compacting hollow-fibre membrane bundles are known in the prior art. They may be, for example, elastic rings which enclose a hollow-fibre bundle at one or more than one place of the hollow-fibre membrane bundle and compact the hollow-fibre membrane bundle according to an applied pre-tension due to the elastic material of the rings. It is further possible for pressure cuffs or pressure pads to be placed around the hollow-fibre membrane bundle or introduced into the hollow-fibre membrane bundle so that pressurization of the pressure cuff or of the pressure pad serves to increase the packing density of the hollow-fibre membranes in the hollow-fibre membrane bundle. It may more particularly also be provided that the hollow-fibre membrane bundle by virtue of a special geometry given to the housing or parts of the housing, in particular by virtue of at least one liquid inlet or by virtue of at least one liquid outlet are shifted out of their position and brought into a compressed state in order thereby to compress at least part of the hollow-fibre membrane bundle. This may be accomplished, for example, by means of a mandrel and/or a sleeve introduced into the centre of the hollow-fibre membrane bundle and parallel to the longitudinal axis of the housing.

Preferably, the at least one compression apparatus is designed to be capable of compressing at least that subregion of the hollow-fibre membrane bundle that adjoins the first open end.

A further step of the method according to the invention comprises introducing the hollow-fibre membrane bundle into the housing by the first end of the hollow-fibre membrane bundle having the terminally open lumens of the hollow-fibre membranes being oriented towards the at least one first liquid inlet at the first end of the housing. In this arrangement of the introduced hollow-fibre membrane bundle, the liquid inlet and the open ends of the lumens of the hollow-fibre membranes are arranged adjacently so that there is a liquid communication between inflowing liquid and the open lumens of the hollow-fibre membranes and the inflowing liquid is capable of penetrating into the interior of the hollow-fibre membranes through the open lumens.

The step of introducing the hollow-fibre membrane bundle into the housing may be effected using a low-friction interfoil in which a hollow-fibre membrane bundle to be tested has been wrapped. The hollow-fibre membrane bundle wrapped in the foil has a lower diameter than the housing inside diameter, so the wrapped hollow-fibre membrane bundle is pushable into the housing. The low-friction foil between the housing inside wall and the hollow-fibre membrane bundle can subsequently be pulled out to leave the hollow-fibre membrane bundle in the housing. Preference is given to an embodiment wherein the hollow-fibre membrane bundle is introduced into the housing in a partially compressed state. Inside the housing itself, the hollow-fibre membranes align in a substantially space-filling manner in accordance with the compressive stress of the hollow-fibre membrane bundle and relax. For the purposes of the present invention, the step of introducing a hollow-fibre membrane bundle into a housing whilst the hollow-fibre membrane bundle is under compressive stress such that the hollow-fibre membranes largely fill out the space of the housing is also referred to as a step of "impressing" the hollow-fibre membrane bundle into the housing.

A further step of the method according to the invention comprises providing a test liquid. For the purposes of the present invention, the term "test liquid" is to be understood as meaning a liquid with which a membrane can be tested as regards a permeation property. Such test liquids may be, for example, aqueous solutions, pure water, blood plasma or blood. The test liquid or at least a part of it is membrane permeant. The term "membrane permeant" herein is to be understood as meaning that the test liquid or a part thereof is able to permeate from the lumen of the hollow-fibre membrane through the membrane wall and into the outer surroundings of the hollow-fibre membrane.

The test liquid is preferably provided in a reservoir with or without temperature regulation. In principle, any choice of temperature is suitable for carrying out the method of the invention. Particularly temperatures from 10° C. to 90° C. are conceivable for carrying out the method. More particularly, temperatures from 20° C. to 40° C. are also envisaged for carrying out the method.

A further step of the method according to the invention comprises routing at least one first test liquid through the at least one liquid inlet at the first end of the housing into the interior of the housing and/or of the hollow-fibre membrane bundle and/or of the hollow-fibre membranes. As a result of this operation, the interspace between the hollow-fibre membranes as well as the lumens of the hollow-fibre membranes are flushed through to an at least partial extent, preferably to an essentially complete extent.

A further step of the method according to the invention comprises compressing the hollow-fibre membrane bundle located in the housing in at least a subregion of the hollow-fibre membrane bundle, by means of the at least one compression apparatus. More particularly compressing the hollow-fibre membrane bundle subregion adjoining the first end of the hollow-fibre membrane bundle. The compression causes an increase in the packing density of the hollow-fibre membranes in this subregion versus the uncompressed subregion of the hollow-fibre membrane bundle. The compression thereby also gives rise to a flow resistance in the interspace between the hollow-fibre membranes. It is provided that the degree of compression is such that any flow of liquid is substantially stopped in the interspace between the hollow-fibre membranes. The compressed subregion of the hollow-fibre membrane bundle in this case causes inflowing liquid to penetrate at the first end of the housing into the interior of the housing and into the open lumens of the hollow-fibre membranes and the penetration of the liquid into the interspace between the hollow-fibre membranes to be impeded or stopped.

The degree of compression must not be so severe as to damage hollow-fibre membranes; more particularly, the space for liquid in the lumens of the hollow-fibre membranes must not be impaired. Some deformation of the hollow-fibre membranes is tolerable, however. The measure for determining the compression of the hollow-fibre membrane bundle for a given number and geometry of the hollow-fibre membranes is the packing density. It was found that a packing density of at least 80% in the compressed subregion of the hollow-fibre membrane bundle is effective in stopping the flow between the hollow-fibre membranes at the test liquid entry pressures envisaged for the method of the invention. At packing densities above 150%, there is already some risk of damage to the hollow-fibre membranes, depending on the membrane material. The packing densities in the compressed subregion of the hollow-fibre membrane bundle are preferably in the range from above 80% to 150%, more preferably in the range from 85% to 120% and yet more preferably in the range from 90% to 110%. The packing density in the uncompressed subregion of the hollow-fibre membrane bundle differs versus the compressed subregion, since a flow of liquid in the space between the hollow-fibre membranes is required in this subregion. Packing densities in the uncompressed subregion may be in the range from more than 20% to less than 70%. For a given necessary pressure of the inflowing test liquid, a packing density above 70% is already sufficient to adversely hinder the flow between the hollow-fibre membranes.

A further step of the method according to the invention comprises determining the permeation property, more particularly the ultrafiltration rate and/or the ultrafiltration coefficient of the hollow-fibre membranes by measuring a value, more particularly the test liquid quantity generated at one or more than one liquid outlet, specifically per unit time and based on the transmembrane pressure difference.

The term "permeation property" of a membrane herein refers to that characteristic of a transmembrane type mass transfer which relates to a permeation of a fluid through a membrane wall. A permeation property of a membrane provides information about the pore structure of the membrane and is taken as a metric capable of characterizing the membrane as regards its porous structure. Any permeation observed as a result of the transmembrane type mass transfer is generally considered in relation to further quantities. More particularly, the term is herein also to be understood as meaning how much liquid can be separated off in a time interval by permeation through the membrane. The amount of permeated liquid per unit time corresponds to the ultrafiltration rate. If the ultrafiltration rate is in turn related to the transmembrane pressure difference, this permeation value indicates the ultrafiltration coefficient. For the purposes of the present invention, the ultrafiltration rate and the ultrafiltration coefficient are each taken as a permeation property descriptive of a hollow-fibre membrane.

A more particular finding in relation to one embodiment of the invention was that the method of the invention is useful for determining the ultrafiltration rate, more particularly the ultrafiltration coefficient of the hollow-fibre membranes tested. A requirement for determining the ultrafiltration rate is that the inflowing test liquid impinging on the end of the hollow-fibre membrane bundle with the terminally unclosed hollow-fibre membranes should flow essentially only into the lumen of the hollow-fibre membranes and not into the interspace between the hollow-fibre membranes. This may be accomplished, as described above, by the hollow-fibre membrane bundle comprising the region of the terminally unclosed hollow-fibre membranes being compressed. The compressed region of the hollow-fibre membrane bundle thereby constitutes a "quasi-encapsulation". As a result, the compression of the hollow-fibre membrane bundle emulates the functionality of a potting resin encapsulating the hollow-fibre membrane bundle by only allowing a stream of liquid in the interior of the hollow-fibre membranes. The flow of liquid between the fibres in the compressed region of the hollow-fibre membrane bundle, by contrast, is severely impeded or impossible. The higher the degree of compression, the lower the flowrate in the space between the hollow-fibre membranes.

The test liquid entering through the open ends of the hollow-fibre membranes flows through the interior of the hollow-fibre membranes. Since the ends of the hollow-fibre membranes at the second end of the hollow-fibre membrane bundle are closed, the test liquid will permeate in the uncompressed part of the hollow-fibre membrane bundle through the membrane wall, as a so-called ultrafiltrate, into the space between the hollow-fibre membranes. The space between the hollow-fibre membranes communicates with the one further liquid outlet, making it possible to route the ultrafiltrate away out of the housing.

In a further embodiment according to the first aspect of the invention, a permeation property of the hollow-fibre membrane, more particularly the ultrafiltration rate and/or the ultrafiltration coefficient is recorded by multiply or continuously measuring a measured value, more particularly the liquid quantity generated at one or more than one liquid outlet during the step of inflowing the at least one test liquid into the housing in a time-dependent manner in order to obtain a time-dependent trajectory of measured values. The multiplicity of the time-dependently recorded measurements or the continuous trajectory of measured values is useful to rectify variations due to experimental error. Provided other parameters of the experimental procedure, for example the temperature or transmembrane pressure difference, are kept constant, a linear correlation is obtained for the recorded ultrafiltrate quantity as a function of time. Correspondingly, a linear regression can be fitted to the trajectory of measured values and the ultrafiltration rate determined from the slope. The ultrafiltration coefficient is derivable by normalization to the pre-set constant transmembrane pressure difference.

In a further embodiment according to the first aspect of the invention, the compressed part of the hollow-fibre membrane bundle extends axially over a longitudinal portion of 10 mm to 150 mm measured from the first end of the hollow-fibre membrane bundle. Below a length of 10 mm, the compression of the hollow-fibre membrane bundle, depending on the packing density of the hollow-fibre membranes, delivers an insufficient effect to stop the flow of the test liquid in the space between the hollow-fibre membranes. Above a length of 150 mm, the meaningfulness of the measured results as a quality feature for the construction of haemodialysers degrades, since the hollow-fibre membrane bundles in the manufacture of dialysis filters themselves have but a length of about 250 mm to 300 mm. When the region where the ultrafiltration of the hollow-fibre membrane takes place is too small, the measuring procedure is liable to have an undesirable breadth of error.

In a further embodiment according to the first aspect of the invention, the at least one liquid outlet has a first opening and a second opening and the liquid outlet is mounted on the housing so as to establish a liquid communication between the first opening, which resides in the uncompressed part of the hollow-fibre membrane bundle, and the second opening, which resides outside the hollow-fibre membrane bundle, while the liquid outlet more particularly extends through the compressed subregion of the hollow-fibre membrane bundle.

More particularly, the at least one liquid outlet in one embodiment is constructed on the housing so as to penetrate through the hollow-fibre membrane bundle at the first end with the terminally open hollow-fibre membranes, in axial orientation of the hollow-fibre membranes, and compresses the hollow-fibre membrane bundle in this part of the hollow-fibre membrane bundle. It is envisaged for this embodiment that the liquid outlet takes the form of a sleeve. At the same time, in this embodiment, the liquid outlet serves as compression apparatus for the hollow-fibre membrane bundle by displacing the hollow-fibre membranes in the corresponding portion of the hollow-fibre membrane bundle and thus brings about a higher packing density. In this embodiment, therefore, the liquid outlet establishes a liquid communication with the space between the hollow-fibre membranes in the uncompressed part of the hollow-fibre bundle in order to route away ultrafiltrate generated there.

In order to perform the functions of compression and liquid outlet at one and the same time, a further embodiment according to the first aspect of the invention provides that the liquid outlet be accommodated on the housing in a mobile manner. In a further step of the method according to the invention, the liquid outlet is moved axially to the longitudinal axis of the housing and pushed into a portion of the hollow-fibre membrane bundle, so the hollow-fibre membranes are displaced out of their position and the packing density increases. The insertion of the liquid outlet into the hollow-fibre membrane bundle may be effected by means of an auxiliary. The auxiliary may be left in the hollow-fibre membrane bundle or removed again after the liquid outlet has been inserted.

This embodiment provides that the liquid outlet be configured in mandrel form or that the liquid outlet be configured as a sleeve, which is pushed into the hollow-fibre membrane bundle by means of a mandrel. A mandrel-shaped geometry has the effect that the hollow-fibre membranes can be displaced to increase the packing density in the compression region without their suffering any damage in the process.

A further embodiment provides that the compression of the hollow-fibre membrane bundle be produced using a combination of various compression apparatuses. It may accordingly be provided to produce some of the compression using for pushing into the hollow-fibre membrane bundle a sleeve formed of a liquid outlet and elastic rings or a pressure cuff.

The packing density in the uncompressed part of the hollow-fibre bundle is envisaged to be less than 70%. In the context of the terminology used in the present invention, the terms "compressed" and "uncompressed" refer to portions of the hollow-fibre membrane bundle which have different packing densities relative to each other. The terms are not necessarily to be understood as absolute terms. Accordingly, a hollow-fibre bundle portion having a packing density of 60% can be taken as uncompressed and a second portion of the hollow-fibre membrane bundle has a packing density of 80%.

A further embodiment according to the first aspect of the invention provides that the housing is equipped with at least one opening for deaeration. Complete deaeration of the interior space of the housing may be necessary for reproducibility of the ultrafiltration measurement. Accordingly, one step of the method according to the first aspect of the invention comprises that air displaced during the inflow of the test liquid into the housing be routed away via the gas outlet. Depending on the pore constitution of the hollow-fibre membranes tested, the routing away of displaced air may be necessary if it cannot be completely routed out of the housing via the liquid outlet. The deaeration opening of the housing may take for example the form of a hole circle on the housing. The deaeration opening is positioned directly adjacent the hollow-fibre membrane bundle end whose hollow-fibre membranes are terminally closed. The deaeration opening may be closed again after conditioning, i.e. after the housing has been deaerated.

A further embodiment according to the first aspect of the invention provides at least one further opening in the housing opposite the uncompressed portion of the impressed hollow-fibre membrane bundle and directly adjacent the compressed portion of the hollow-fibre membrane bundle. The openings can be used to route a stream of auxiliary air into the housing during the ultrafiltration measurement in order that ultrafiltrate, which collects circumferentially around the hollow-fibre membrane bundle, be routed away in the direction of the open end of the liquid outlet.

A further embodiment according to the first aspect of the invention provides at least one further liquid outlet on the housing opposite the compressed portion of the impressed hollow-fibre membrane module and directly adjacent the uncompressed portion of the hollow-fibre membrane bundle. The liquid outlet may be of assistance during the conditioning step, i.e. during the flushing through of the housing with test liquid before the start of measurement, in achieving even in the compressed part a complete degree of flushing through in the compressed portion of the hollow-fibre membrane bundle. In addition, this liquid outlet allows for any removal of leakage liquid during the measurement. The term "leakage liquid" herein is to be understood as meaning test liquid which the compression of the hollow-fibre membrane bundle notwithstanding penetrates into the interspace between the hollow-fibre membranes. It is undesirable for leakage liquid to be able to advance as far as into the uncompressed part of the hollow-fibre membrane bundle because there it may be able to distort the measured quantity of ultrafiltrate. The further liquid outlet establishes a communication with the ambient pressure. Therefore, the pressure in the interspace between the hollow-fibre membranes in the compressed subregion of the hollow-fibre membrane bundle decreases to the level of the ambient pressure. The uncompressed subregion is likewise in communication with the ambient pressure, via at least one liquid outlet. Accordingly, any leakage liquid arising in the space between the hollow-fibre membranes in the compressed subregion of the hollow-fibre membrane bundle cannot advance via the further liquid outlet into the uncompressed subregion of the hollow-fibre membrane bundle because the pressure levels are equalized via the further liquid outlet.

A further embodiment of the method according to the invention provides that the compression of the hollow-fibre membrane bundle in a subregion is effected via at least two compression apparatuses. In a further embodiment, one or more, more particularly two, compression apparatuses may be fitted in the interior of the hollow-fibre membrane bundle. A further embodiment may provide one or more compression apparatuses enclosing the hollow-fibre membrane bundle at least partly and one or more compression apparatuses situated in the interior of the hollow-fibre membrane bundle.

Compression due to two compression apparatuses has proved advantageous particularly in measurement methods on hollow-fibre membranes having a large average pore size and a high ultrafiltration coefficient. The occurrence of leakage liquid in the compressed subregion of the hollow-fibre membrane bundle may also be due to ultrafiltration in the compressed subregion in the case of such hollow-fibre membranes in particular. A second compression apparatus works as an improved barrier against the penetration of leakage liquid into the uncompressed subregion of the hollow-fibre membrane bundle.

A further embodiment of the method according to the invention provides that the at least one further liquid outlet is mounted on the housing between the at least two compression apparatuses. As a result, leakage liquid occurring from the direction of the inflowing liquid at the liquid inlet of the housing downstream of the first compression apparatus is removed in an effective manner. In addition, the pressure level in the space between the hollow-fibre membranes downstream of the first compression apparatus is equalized to ambient pressure level. The second compression apparatus additionally prevents further leakage liquid in the compressed subregion being able to advance into the uncompressed subregion of the hollow-fibre membrane bundle.

A further embodiment of the first aspect of the invention provides that the pressure of the inflowing liquid be set at from 50 mbar to 500 mbar, alternatively at from 100 to 300 mbar, alternatively at from 150 to 250 mbar. It transpires that the above-described compression of the hollow-fibre membrane bundle is sufficiently high to cause, at the recited pressures of the incoming test liquid, an adequate blocking effect to flow in the space between the hollow-fibre membranes. The pressures may accordingly be chosen at a sufficiently high level in order to produce a sufficiently high transmembrane pressure gradient for determining the ultrafiltration rate. The ultrafiltration rate is subsequently determinable from the amount/volume of ultrafiltrate isolated per unit time at the liquid outlet. The volume of the ultrafiltrate is determinable according to common procedures volumetrically or gravimetrically based on the density of the test liquid.

It may be the case in certain embodiments, for example because of the number of hollow-fibre membranes in the housing, the hollow-fibre membrane diameter or the pore constitution of the hollow-fibre membranes, that the present method as per an embodiment according to the first aspect of the invention yields values for the ultrafiltration rate which differ from standardized methods, as for example of DIN/EN/ISO 8637:2014. In these cases, the measured values obtained are correctable by means of previously determined calibration values or by means of a calibration function.

To determine calibration values and/or a calibration function, different hollow-fibre membrane filter modules comprising hollow-fibre membranes differing in pore constitution are tested to DIN/EN/ISO 8634 as regards the ultrafiltration coefficient. This is followed by using the method of the invention to determine corresponding hollow-fibre membrane bundles comprising hollow-fibre membranes identical to the hollow-fibre membranes of the respective hollow-fibre membrane filter modules. It was found that the results from the method of the invention can be correlated to the values derived on hollow-fibre membrane filter modules by the prior art procedures and that a calibration curve can be established. In the event that the measurements by the procedure of the invention lead to a systematic difference from other measuring procedures specifically the procedure of DIN/EN/ISO 8637, the present method of the invention accordingly allows for the measured values to be adjusted using a correction function.

In a second aspect, the invention provides an apparatus for carrying out a method according to any of the embodiments according to the first aspect of the invention. The apparatus comprises a measuring apparatus useful for determining a permeation property, more particularly the ultrafiltration rate and/or the ultrafiltration coefficient of hollow-fibre membranes on a hollow-fibre membrane bundle. The apparatus comprises:

- at least one reservoir for receiving a test liquid,
- a housing having a first end and a second end for receiving a hollow-fibre membrane bundle, wherein the first end of the housing has at least one liquid inlet,
- at least one communication apparatus, more particularly pumping means, for feeding the at least one test liquid from the at least one reservoir into the interior of the housing and/or of the hollow-fibre membrane bundle and/or of the hollow-fibre membranes,
- at least one compression apparatus for compressing at least a subregion of the hollow-fibre membrane bundle,
- at least one liquid outlet,
- means for time-dependently measuring a permeation property, more particularly the ultrafiltration rate and/or ultrafiltration coefficient at one or more than one liquid outlet.

The apparatus of the invention offers the advantage that hollow-fibre membrane bundles can be tested as regards their permeation property, more particularly as regards the ultrafiltration rate and/or the ultrafiltration coefficient, without the hollow-fibre membrane modules having to be potted into test filter modules and having to be built up into filter modules. The apparatus of the invention makes it possible to measure hollow-fibre membrane bundles as regards one of their permeation properties, more particularly as regards the ultrafiltration rate and ultrafiltration coefficient, in the course of a few minutes.

The apparatus is therefore very useful for monitoring, in the continuous production of hollow-fibre membranes, the product specifications of the hollow-fibre membrane products as regards any of the predetermined permeability properties.

In a further embodiment of the apparatus according to the invention, the apparatus further comprises means for determining the pressure at one or more than one liquid inlet. Appropriate means are known in the prior art and may for example constitute a pressure sensor. The entry pressure of the inflowing test liquid at the at least one liquid inlet can be determined by means of the pressure sensor. Together with a pump pumping the test liquid to the at least one liquid inlet, a predetermined pressure can be established for the inflowing test liquid. Optionally there may be provided a further means for determining the pressure, more particularly a pressure sensor, on the at least one further liquid outlet in order to quantify the precise transmembrane pressure difference. The pressure at a liquid outlet generally corresponds to the ambient pressure, so to quantify the transmembrane pressure difference it is sufficient to use the recorded pressure value at the at least one liquid inlet. The quantification of the transmembrane pressure difference is necessary for determining the ultrafiltration coefficient from the ultrafiltration rate measured.

Advantageously, in a further embodiment of the apparatus according to the invention, the housing has at least one gas outlet in a terminal part provided for receiving the portion of the hollow-fibre membrane bundle having the terminally closed hollow-fibre membranes. The gas outlet may serve as deaeration opening wherethrough air segregated during the measuring operation can be routed away.

In a further embodiment of the apparatus according to the invention, a portion of the housing that is provided to receive an uncompressed part of the hollow-fibre membrane bundle has at least one opening as gas inlet. The gas inlet may be useful if it is desired to route air into the interior of the housing. The air routed in can be used to produce an airstream in the housing in order to route away generated permeate, more particularly ultrafiltrate in the interspace between the hollow-fibre membranes to the liquid outlet. The precision of the measurement improves the better the separation achievable between the streams of water on the respective membrane sides. It is accordingly important that ideally the entire ultrafiltrate is routed inwardly to the central liquid outlet.

The invention in a third aspect more particularly provides for the use of an apparatus according to the second aspect of the invention in a method according to the first aspect of the invention.

In a fourth aspect, the invention relates to a method of forming hollow-fibre membrane filter modules, wherein the method of the invention according to an embodiment of the first aspect of the invention is used to form hollow-fibre membranes having a predetermined permeation property.

The method of forming hollow-fibre membrane filter modules in the manner of the invention comprises the steps of (a) defining one or more value ranges for at least one permeation property, more particularly the ultrafiltration rate and/or the ultrafiltration coefficient, of hollow-fibre membranes envisaged for forming hollow-fibre membrane filter modules,
(b) selecting one or more manufacturing parameters to form hollow-fibre membranes having the at least one permeation property or the two or more permeation properties, using the value range defined in step (a),
(c) forming hollow-fibre membranes by a spinning process according to one or more manufacturing parameters selected in step (b),
(d) bundling the resulting hollow-fibre membranes into hollow-fibre membrane bundles,
(e) practicing a method according to an embodiment of the first aspect of the invention of determining one or more permeation properties, more particularly the ultrafiltration rate and/or the ultrafiltration coefficient of hollow-fibre membranes according to an embodiment of the first aspect of the invention,
(f) using the hollow-fibre membrane bundles for the construction of filter modules once it has been ascertained that the one or more permeation properties fall within the value range defined in step (a).

Since the method of the invention according to the first aspect of the invention provides a quick way to determine a permeation property, in particular the ultrafiltration rate and/or the ultrafiltration coefficient of the hollow-fibre membranes formed, prompt control also becomes possible for the process of forming hollow-fibre membrane filter modules. More particularly, the hollow-fibre membranes formed can be tested for compliance with the mandated product specification to see whether they can be approved for use in the construction of hollow-fibre membrane filter modules.

Where the hollow-fibre membranes formed by the manufacturing process are found to be off-spec or only just on-spec, appropriate deductions can be made regarding the manufacturing parameters. The manufacturing parameters can subsequently be adjusted such that the hollow-fibre membranes obtained are back on-spec. The manufacturing process thus regulated then reiterates the envisaged steps (a) to (f) by making it possible to decide that the hollow-fibre membranes formed be used for the construction of hollow-fibre membrane filter modules.

The method of forming hollow-fibre membrane filter modules in the manner of the invention is very useful for the formation of hollow-fibre membrane filter modules formed on the basis of the membrane materials polysulphone (PSU) and polyvinylpyrrolidone. The spinning solutions used for forming such hollow-fibre membranes contain polysulphone (PSU) and polyvinylpyrrolidone (PVP) dissolved in a polar aprotic solvent. Examples of suitable solvents include N-methylpyrrolidone, dimethyl sulphoxide and dimethylacetamide. It has been determined that batches of polysulphone/polyvinylpyrrolidone spinning solutions make it particularly difficult to establish the permeation properties, more particularly the ultrafiltration rate and/or the ultrafiltration coefficient, of hollow-fibre membranes in a precise manner, since these respond in a very sensitive manner to variations in production parameters. The present production method of the invention has been determined to be particularly advantageous for forming PSU/PVP hollow-fibre membranes because it allows deviations caused by a change in the production parameters to be detected within a very short time and for the manufacturing process to be adjusted accordingly.

DESCRIPTION OF THE INVENTION WITH REFERENCE TO FIGURES

FIG. 1 is a schematic depiction of an inventive for determining the ultrafiltration rate and/or the ultrafiltration coefficient of hollow-fibre membranes or a hollow-fibre membrane bundle. The measuring apparatus (100) has a measurement chamber (101), a water bath (102) containing temperature-regulated distilled water at 37° C. for use as test liquid, a pump (103) to pump the water into the measurement chamber (101), a flowrate meter (104) and a pressure sensor (105). The pump is closed loop controlled such that the water flowing into the apparatus (100) has a constant entry pressure of 200 mbar. The amount of water supplied is quantified at all times using a flowrate meter (104).

Figure 2:
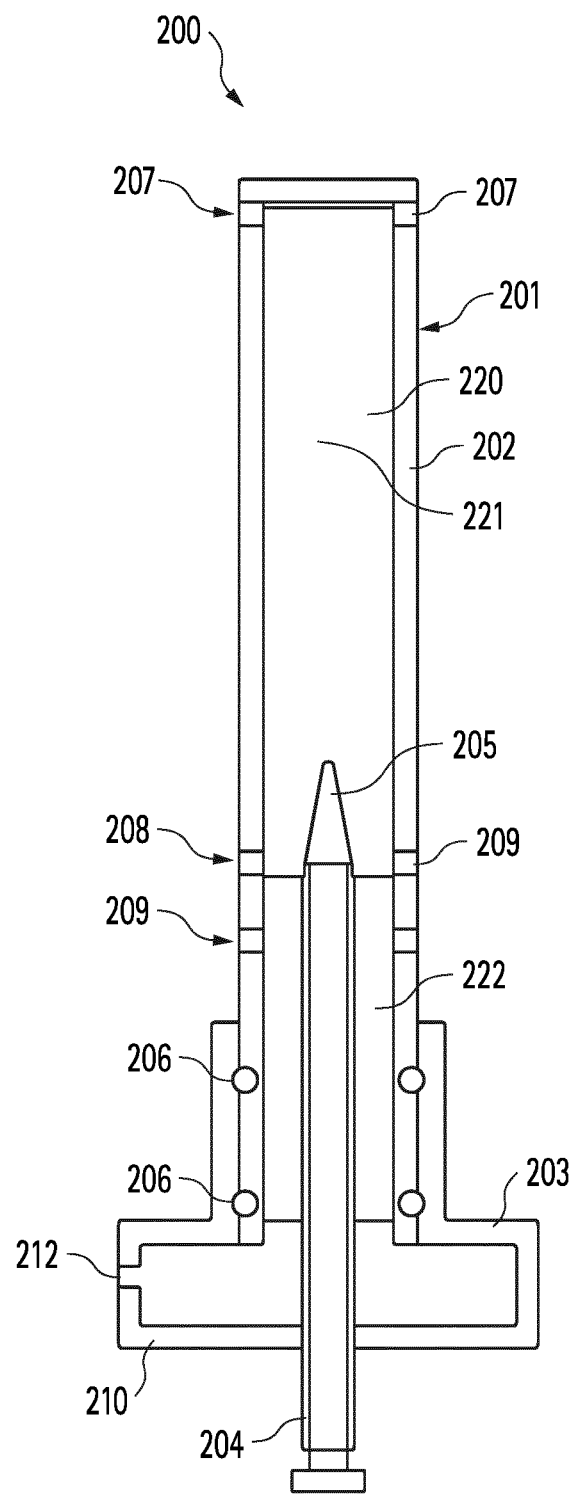

FIG. 2 is a more detailed schematic depiction of the inventive measuring apparatus (200) featuring the following designations:
housing (201)
housing sleeve (202)
receiving part (203)
liquid outlet (204)
mandrel (205)
seal (206)
gas outlet (207)
gas inlet engineered as hole circle (208)
further liquid outlet (209)
floor of the receiving part (210)
hollow-fibre membrane bundle (220)
uncompressed portion of hollow-fibre membrane bundle (221)
compressed portion of hollow-fibre membrane bundle (222)
liquid inlet (212)

A hollow-fibre membrane bundle has been impressed into the housing sleeve (202) of the measurement chamber. The housing in this embodiment consists of a sleeve (202), whereto a receiving part (203) adjoins, and also a sleeve-shaped liquid outlet (204), whereinto a mandrel (205) has been pushed. The receiving part (203) has a liquid inlet (212).

The housing sleeve (202) has been pushed at one end into the receiving part (203) and sealed tight using 2 O-rings (206). The housing is additionally provided 3 hole circles. The hole circles form the gas outlet (207), the gas inlet (208) and the further liquid outlet (209) to remove leakage water. Water is used as test liquid.

At the floor (210) of the receiving part (203) is installed a slideable mandrel (205) with a slideable mandrel (205) where the sleeve enclosing the mandrel is engineered as a liquid outlet (204) which reaches into the fibre bundle (220). The mandrel (205) can be removed again. This leaves the sleeve-shaped liquid outlet (204) inside the hollow-fibre membrane bundle (220).

The hollow-fibre membrane bundle has an uncompressed portion (221) in the upper region, where there is no mandrel (203) and/or liquid outlet (204), and a compressed portion (222) in the lower region.

Figure 3:
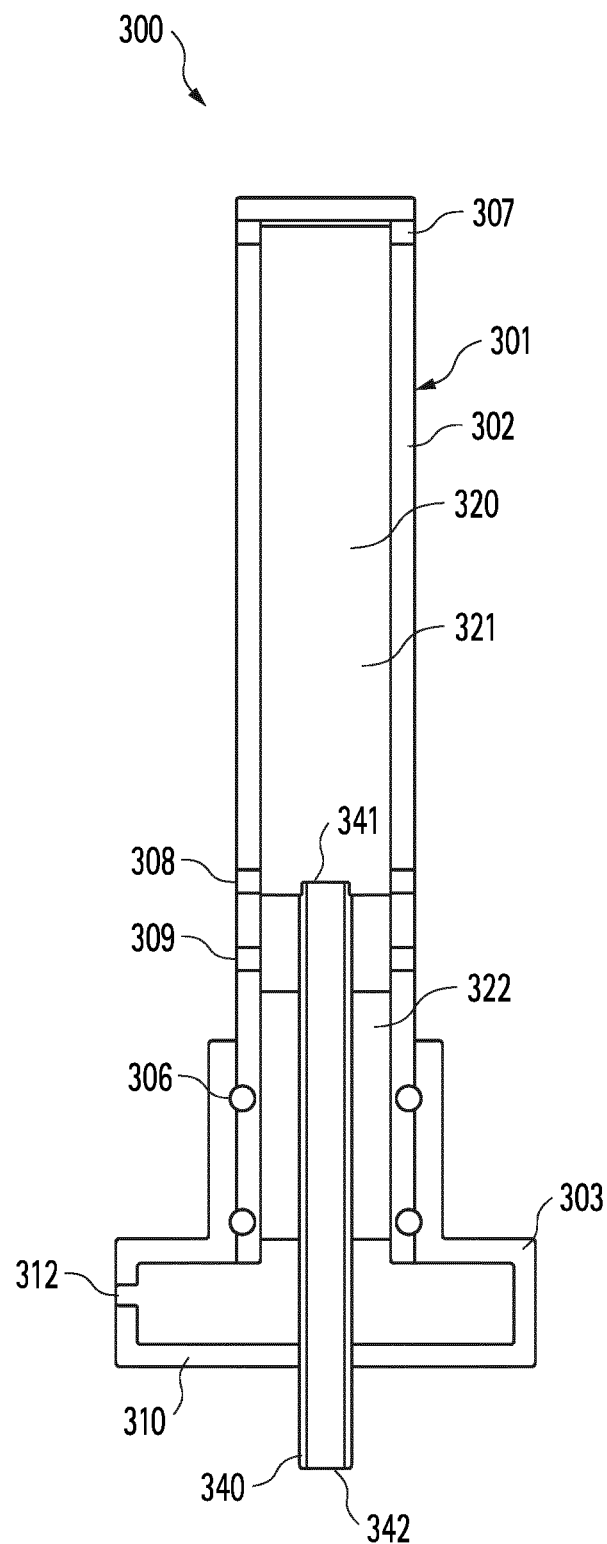

FIG. 3 is a further schematic depiction of an inventive measuring apparatus (300) which is essentially identical to the measurement chamber of FIG. 2. The following designations apply to FIG. 3:
housing (301)
housing sleeve (302)
receiving part (303)
liquid outlet (340)
first end of liquid outlet (341)
second end of liquid outlet (342)
seals (306)
gas outlet (307)
gas inlet (308)
further liquid outlet (309)
floor of receiving part (310)
hollow-fibre membrane bundle (320)
uncompressed portion of hollow-fibre membrane bundle (321)
compressed portion of hollow-fibre membrane bundle (322)
liquid inlet (312)

FIG. 3 shows an embodiment featuring a liquid outlet (340) situated inside the hollow-fibre membrane bundle. A first end (341) of the liquid outlet is located in the uncompressed portion (321) of the hollow-fibre membrane bundle. The second end (341) of the liquid outlet is located outside the measuring apparatus (300), establishing a liquid communication with the space between the hollow-fibre membranes in the uncompressed portion (321) of the hollow-fibre membrane bundle (320) and the outside surface of the measuring apparatus (300). The leakage water leaking out of the lower hole circle (309) of the sleeve is returned into the water reservoir. The auxiliary air can be supplied by means of a cuff on the gas inlet (308). The gas outlet (307) is selectively openable or closable. The ultrafiltrate is weighed using an analytical balance and arithmetically converted, via the density, into millilitres per unit time.

Figure 4:
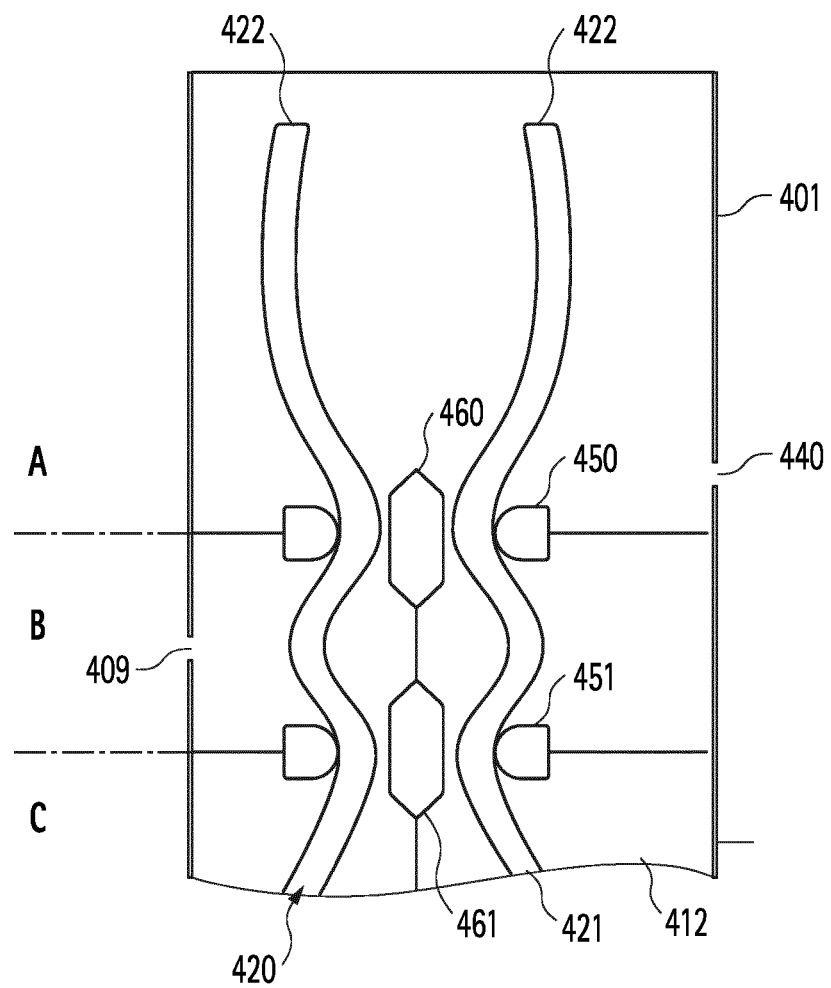

FIG. 4 shows a schematic depiction of a further embodiment of the inventive apparatus, featuring an alternative compression apparatus whereby the flow of test liquid in the space between the hollow-fibre membranes can be stopped. The following designations apply to FIG. 4:
housing (401)
liquid outlet (440)
further liquid outlet (409)
liquid inlet (412)
hollow-fibre membranes (420, 421)
liquid-tightly closed end of hollow-fibre membranes (422)
first compression apparatus (450)
second compression apparatus (451)
third compression apparatus (460)
fourth compression apparatus (461)

FIG. 4 shows two hollow-fibre membranes (420, 421) which are schematically representative of a multiplicity of hollow-fibre membranes of a hollow-fibre membrane bundle and which are liquid-tightly closed at one end (422). FIG. 4 further shows a first compression apparatus (450) and a second compression apparatus (451), which encloses the hollow-fibre membrane. There is further a third compression apparatus (460) installed within the hollow-fibre membrane bundle which is symbolized by the hollow-fibre membranes (420, 421). A fourth compression apparatus (461) is likewise situated within the hollow-fibre membrane bundle. It may be provided in one embodiment that one or more compression apparatuses (450, 451) are installed so as to enclose the hollow-fibre membrane bundle. The wave-shaped drawing of the hollow-fibre membranes (420, 421) is a schematic representation of the compression of the hollow-fibre membrane bundle due to the compression apparatuses (450, 451, 460, 461). The first and third compression apparatuses (450, 460) and also the second and fourth compression apparatuses (451, 461) are installed at essentially the same height on and, respectively, in the hollow-fibre membrane bundle; that is, they are positioned opposite each other.

The four placed compression apparatuses divide the hollow-fibre membrane bundle into three regions (A, B, C). Region C is in communication with the liquid inlet (412). Region A communicates with a liquid outlet (440). Due to the inflowing test liquid, the pressure in the lumen of the hollow-fibre membranes is the pressure from region C. Since the pressure in region C is higher by virtue of the inflowing liquid than in the interspace between the hollow-fibre membranes in region A, test liquid undergoes an ultrafiltration through the membrane wall from the lumen side of the hollow-fibre membranes into the interspace of the hollow-fibre membranes in region C. Compression of the hollow-fibre membrane bundle due to compression apparatus (451) and/or (461) largely stops any flow of inflowing test liquid in the interspace between the hollow-fibre membranes from region C into region B. Any remaining amount of test liquid flowing in the interspace between the fibres into region B or penetrating by ultrafiltration from the lumens in region B into the interspace between the hollow-fibre membranes is leakage liquid and is removed out of the housing via liquid outlet (409). In some embodiments, an accurate measurement requires that the leakage liquid be removed, depending on the amount of leakage liquid generated. A requirement in this case is that region B be divided from region A by a further compression apparatus and region B communicate with a further liquid outlet (409). The further liquid outlet (409) causes a pressure to become established in the interspace between the hollow-fibre membranes that corresponds to the ambient pressure. The pressure prevailing in the interspace between the hollow-fibre membranes in region C corresponds to the ambient pressure via a liquid outlet (440). The pressure in the interspace between the hollow-fibre membranes in regions B and C is essentially the same. It is accordingly impossible for leakage liquid to advance into region C via the further compression apparatus (450) and/or (460). An apparatus according to FIG. 4 has proved advantageous in particular for hollow-fibre membranes having very high ultrafiltration coefficients.

Example 1—Experimental Procedure

The method of the invention will now be described with reference to an example without, however, being limited to this example. The water bath (102) is filled up with distilled water and temperature regulated to 37° C. The fibre bundle to be tested is melted shut on one side by means of an aluminium foil on a hotplate at about 300° C. The thus treated hollow-fibre membrane bundle (220, 320) is impressed into the housing sleeve (201, 301).

The housing sleeve (201, 301) is then introduced into the receiving part (202, 303). The mandrel (205) is pressed together with the sleeve (204, 340) surrounding the mandrel into the fibre bundle (220, 320) as far as it will go. The mandrel (205) is subsequently pulled out, leaving the sleeve (340) inside the bundle.

An air cuff is installed on the hole circle of the gas inlet (208, 308) and a small airstream is routed in. The hole circle of the gas outlet (207, 307) is closed.

The pump is switched on. After conditioning, i.e. after 5 or 10 minutes of pumping, depending on membrane type, the ultrafiltrate is collected in a receptacle for weighing at defined times during the measurement. The ultrafiltration coefficient is computable by means of the transmembrane pressure measured.

Example 2—Principle of Measurement

The ultrafiltration rate is measured directly on the hollow-fibre membrane bundle (220, 320) to be tested without the hollow-fibre membrane bundle first having to be potted and incorporated in a filter module. By way of an alternative to the potted encapsulation present in the filter module, a very strong resistance to flow is produced in the interspace between the hollow-fibre membranes. This largely stops any flow in the region of this flow resistance which corresponds to the compressed part of the hollow-fibre membrane bundle in the housing (222, 322). The flow resistance produced thus delivers the same effect as an otherwise customary potted encapsulation by stopping liquid flow between the hollow-fibre membranes whilst, however, leaving the terminally open hollow-fibre membranes accessible to inflowing liquid, and thereby allowing liquid to enter the lumens of the hollow-fibre membrane bundle.

The hollow-fibre membrane bundle (221, 321) impressed into the housing of the measuring apparatus (100, 200, 300) is flushed through with test liquid for performing a measurement. The test liquid is made to flow in through the liquid inlet (212, 312) into the measuring apparatus (100, 200, 300), in particular into the receiving part of the housing (203, 303) and the entry pressure established at 200 mbar. The entry pressure can be established using pressure sensor (105) and pump (103).

The entry pressure becomes established in the receiving part and on the lumen side of the hollow-fibre membranes along the entire length of the hollow-fibre membrane in the embodiments of FIG. 1 and FIG. 3. The test liquid can only pass through transmembrane transfer into the interspace between the hollow-fibre membranes in the portion of the uncompressed part (321) of the hollow-fibre membrane bundle. This transfer results in the formation of a pressure gradient, so the water pressure prevailing in the interspace between the hollow-fibre membranes in the uncompressed part (321) corresponds to the ambient pressure. The water in the interspace between the hollow-fibre membranes is generated by ultrafiltration and flows through the (340) liquid outlet towards the outside. It is the transmembrane pressure gradient which is responsible for the ultrafiltration.

The precision of the measurement improves the better the separation achievable between the streams of water on the respective membrane sides. It is accordingly important that ideally the entire ultrafiltrate is routed inwardly to the central liquid outlet (304). The water present in the interspaces between the hollow-fibre membranes as a result of ultrafiltration is routed to the central liquid outlet (304). This is effected by means of the gas inlet (308) wherethrough an airstream is routed into the housing. The hole circle for this auxiliary air is installed in the housing sleeve (302) such that the water droplets which may form inside the hollow-fibre membrane bundle (220, 320) are led from out to in towards the first end (341) of the liquid outlet (340) and routed away.

To ensure an intensive and reproducible compression of the bundle, a portion of the impressed hollow-fibre membrane bundle is greatly deformed by means of the mandrel (205) and the sleeve-shaped liquid outlet (204, 340) so as to obtain a maximum resistance to flow between the hollow-fibre membranes without damaging the hollow-fibre membranes. Owing to the displacement of the hollow-fibre membranes, the packing density in the compressed portion of the hollow-fibre membrane in the present example of use increases from about 60% to about 95%.

The invention claimed is:

1. A method of determining at least one permeation property of hollow-fiber membranes, comprising the steps of:
   (a) providing a hollow-fiber membrane bundle comprising a multiplicity of hollow-fiber membranes having a first end and a second end, wherein the lumens of the hollow-fiber membranes at the first end of the hollow-fiber membrane bundle are terminally open, and at the second end of the hollow-fiber membrane bundle are terminally closed,
(b) providing a housing for receiving the hollow-fiber membrane bundle having a first end and a second end, wherein the first end has at least one liquid inlet,
(c) introducing the hollow-fiber membrane bundle into the housing, wherein the first end of the hollow-fiber membrane bundle having the terminally open lumens of the hollow-fiber membranes is oriented towards the at least one liquid inlet at the first end of the housing,
(d) determining a permeation property of the hollow-fiber membranes
the method further comprises the steps of:
(e) providing at least one compression apparatus for compressing the hollow-fiber membrane bundle in at least a subregion of the hollow-fiber membrane bundle,
(f) providing at least one liquid outlet,
(g) providing at least one test liquid,
(h) inflowing the at least one test liquid through the at least one liquid inlet at the first end of the housing into the interior of the housing and/or of the hollow-fiber membrane bundle and/or of the hollow-fiber membranes,
(i) compressing the hollow-fiber membrane bundle in at least a subregion of the hollow-fiber membrane bundle, wherein in step
(d) an ultrafiltration rate, or an ultrafiltration coefficient, or both, of the hollow-fiber membranes are determined by recording at least one measured value.

2. The method according to claim 1, further comprising the step of:
(j) repeatedly recording measured values or continuously recording a measured-value trajectory at one or more than one liquid outlet during the step of inflowing the at least one test liquid into the housing through at least one liquid inlet of the housing.

3. The method according to claim 1, wherein the compressed subregion of the hollow-fiber membrane bundle is in a compressed state such that a liquid stream of the inflowing test liquid between the hollow-fiber membranes is essentially prevented.

4. The method according to claim 1, wherein the packing density of the hollow-fiber membranes in the compressed subregion of the hollow fibre hollow-fiber membrane bundle is more than 80% to 150%.

5. The method according to claim 1, wherein the compression of the hollow-fiber membrane bundle is effected by introducing the at least one compression apparatus into the interior of the hollow-fiber membrane bundle and/or by force exertion onto the exterior of the hollow-fiber membrane bundle by the at least one compression apparatus.

6. The method according to claim 1, wherein the packing density of the hollow-fiber membranes in the uncompressed subregion of the hollow-fiber membrane bundle is less than 70%.

7. The method according to claim 1, wherein leakage liquid in the compressed part of the hollow-fiber membrane bundle is routed away out of the housing through at least one further liquid outlet on the housing.

8. The method according to claim 1, wherein the at least one liquid outlet is a constituent part of the housing or is a constituent part of the at least one compression apparatus.

9. The method according to claim 1, wherein the compression of the hollow-fiber membrane bundle in the compressed subregion is effected via at least two compression apparatuses.

10. The method according to claim 9, wherein the at least one further liquid outlet is mounted on the housing such that any leakage liquid arising between the at least two compression apparatuses is routed away.

11. The method according to claim 1, wherein there is further at least one gas inlet and at least one gas outlet present on the housing and/or the at least one compression apparatus.

12. The method according to claim 11, wherein the gas, enters through the at least one gas inlet, wherein the entering gas flows through the interspaces between the hollow-fiber membranes of the hollow-fiber membrane bundle and may optionally exists again from the interspaces between the hollow-fiber membranes of the hollow-fiber membrane bundle at least partly through the at least one gas outlet.

13. The method according to claim 1, wherein the at least one inflowing test liquid is routed into the interior of the housing and/or of the hollow-fiber membrane bundle at an inlet pressure of 50 mbar to 500 mbar.

14. The method according to claim 13, wherein the pressure of the test liquid in the lumens of the hollow-fiber membranes corresponds to the inlet pressure of the at least one test liquid along the entire length of the hollow-fiber membranes.

15. The method according to claim 1, wherein the test liquid present in the interspaces of the hollow-fiber membrane downstream of the at least first liquid outlet is essentially test liquid which has passed out of the lumens of the hollow-fiber membranes and through the hollow-fiber membrane.

16. The method according to claim 1, wherein the hollow-fiber membrane bundle is unclosed.

17. An apparatus for carrying out the method according to claim 1, comprising:
(a) at least one reservoir for receiving at least one test liquid,
(b) a housing having a first end and a second end for receiving a hollow-fiber membrane bundle, wherein the first end of the housing has at least one liquid inlet,
(c) at least one communication apparatus for feeding the at least one test liquid from the at least one reservoir into the interior of the housing and/or of the hollow-fiber membrane bundle hollow-fiber membranes,
(d) at least one compression apparatus for compressing at least a subregion of the hollow-fiber membrane bundle,
(e) at least one liquid outlet,
(f) means for time-dependently measuring a permeation property.

18. The apparatus according to claim 17, wherein the apparatus further comprises means for determining the pressure at one or more than one liquid inlet of the housing.

19. The apparatus according to claim 17, wherein the apparatus comprises at least one gas inlet and at least one gas outlet.

20. A method of forming hollow-fiber membrane filter modules, comprising the steps of:
(a) defining one or more value ranges for at least one or more permeation properties of hollow-fiber membranes envisaged for forming hollow-fiber membrane filter modules,
(b) selecting one or more manufacturing parameters to form hollow-fiber membranes having the at least one permeation property or the two or more permeation properties, using the value range defined in step (a),
(c) forming hollow-fiber membranes by a spinning process according to one or more manufacturing parameters selected in step (b),
(d) bundling the resulting hollow-fiber membranes into hollow-fiber membrane bundles,
(e) practicing a method of determining one or more permeation properties according to claim 1,
(f) using the hollow-fiber membrane bundles for the construction of hollow-fiber membrane filter modules once it has been ascertained that the one or more permeation properties fall within the value range defined in step (a).

21. The method of forming hollow-fiber membrane filter modules according to claim 20, further comprising adapting the at least one or more selected manufacturing parameters from step (b), if it is found that the one or more permeation properties of the hollow-fiber membranes formed do not fall within the one or more value ranges defined in step (a) so that, in accordance with the step of adapting the manufacturing parameters, the permeation properties of hollow-fiber membranes formed are back within the value range defined in step (a).

* * * * *